United States Patent [19]
Ferguson

[11] Patent Number: 4,583,976
[45] Date of Patent: Apr. 22, 1986

[54] CATHETER SUPPORT

[75] Inventor: Keith T. Ferguson, Scotch Plains, N.J.

[73] Assignee: E. R. Squibb & Sons, Inc., Princeton, N.J.

[21] Appl. No.: 615,624

[22] Filed: May 31, 1984

[51] Int. Cl.⁴ ............................................. A61M 25/02
[52] U.S. Cl. .............................. 604/174; 128/DIG. 26
[58] Field of Search ................................ 604/174–180; 128/DIG. 26, 133, DIG. 15

[56] References Cited

U.S. PATENT DOCUMENTS

| 3,146,788 | 9/1964 | Mahlstedt et al. |
| 3,339,546 | 9/1967 | Chen |
| 3,630,195 | 12/1971 | Santomieri |
| 3,677,250 | 7/1972 | Thomas |
| 3,726,280 | 4/1973 | Lacount |
| 3,765,421 | 10/1973 | Poprik |
| 3,826,254 | 7/1974 | Mellor |
| 3,834,380 | 9/1974 | Boyd |
| 3,878,849 | 4/1975 | Muller et al. |
| 4,096,863 | 6/1978 | Kaplan et al. |
| 4,122,857 | 10/1978 | Haerr |
| 4,192,785 | 3/1980 | Chen et al. |
| 4,324,237 | 4/1982 | Buttaravoli |
| 4,333,468 | 6/1982 | Guist ............................ 604/180 |
| 4,393,080 | 7/1983 | Pawelchak |
| 4,416,664 | 11/1983 | Womack |
| 4,445,894 | 5/1984 | Kovacs |
| 4,457,754 | 7/1984 | Buttaravoli |
| 4,484,914 | 11/1984 | Brown |

FOREIGN PATENT DOCUMENTS 0092999  4/1983  European Pat. Off. .

Primary Examiner—Stephen C. Pellegrino
Attorney, Agent, or Firm—L. S. Levinson; R. E. Lee, Jr.

[57] ABSTRACT

A catheter support comprising an anchoring pad and a flexible strap, a portion of which is attached thereto, is disclosed. One side of the anchoring pad carries an adhesive compatible for use with human skin. One side of the strap carries a fastener material. With the pad in place, a catheter is laid against the pad, and the free end of the strap is folded across the catheter. The fastener material of the free end is pressed against the fastener material attached to the pad to hold the catheter in place. Alternatively, the side of the pad opposite the side with the adhesive carries fastener material, and the flexible strap is separate therefrom. A channel is present through the fastener material on either the pad, flexible strap or both to receive the catheter.

5 Claims, 6 Drawing Figures

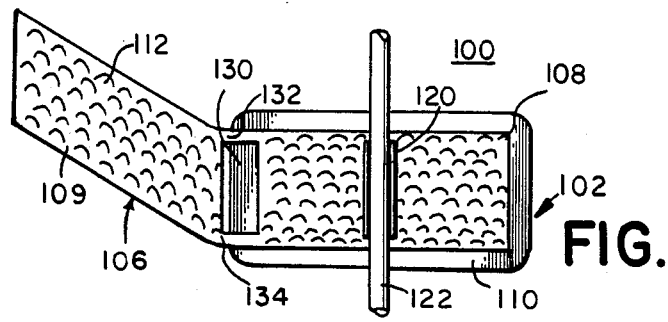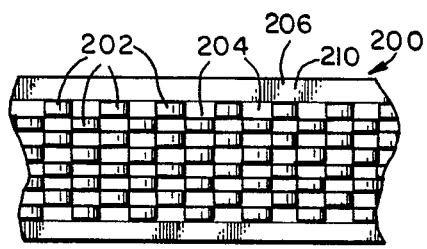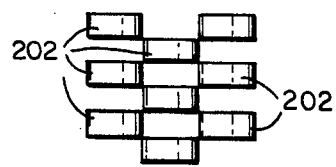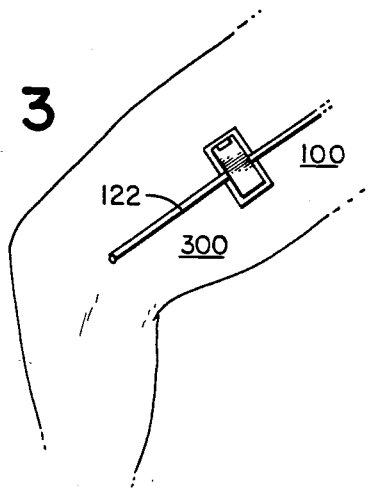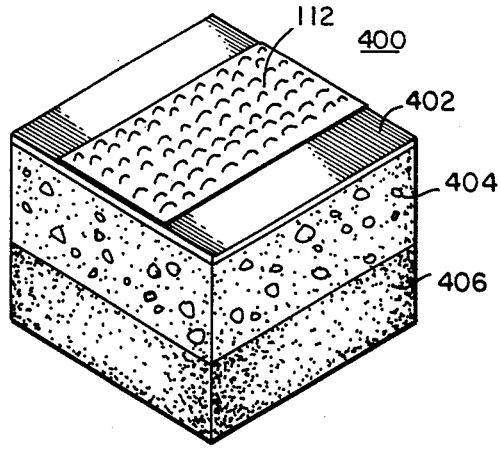

CATHETER SUPPORT

BACKGROUND OF THE INVENTION

This invention relates to devices for securing therapeutic appliances to living bodies, particularly for holding catheters in place on the body.

Indwelling or "Foley" type catheters used for draining body cavities are often used by ambulatory patients for extended periods of time. It is important that such catheters be held securely in place to avoid irritation and discomfort for the patient due to local movement of the catheter when the patient is moving. At the same time any device used for securing the catheter should itself be comfortable to wear, easy to use, and universal in size to accomodate different patients.

Prior art securing devices are disclosed in U.S. Pat. Nos. 3,726,280; 3,765,421; 3,878,849; 4,096,863 and 4,416,664. Each of these patents teaches the use of a strap for encircling the limb where the catheter is to be secured. The strap is fastened using fastener material such as VELCRO TM or by snap fasteners, for example. A retainer strap is fastened at one end to the flexible strap such as by stitching while the free end of the retainer strap is crossed over the tube or catheter to hold it in place. The free end is secured to the strap using fastener material such as VELCRO TM or by snap fasteners. U.S. Pat. No. 4,416,604 further discloses the use of a pad member secured to the limb by a limb encircling flexible strap. The catheter is secured against the pad in a manner similar to that described above.

SUMMARY OF THE INVENTION

An object of the present invention is to provide an improved catheter support.

Another object of the present invention is to provide the above described support which is comfortable to wear and easy to use.

A further object of the present invention is to provide the above described support which is universal in size.

The present invention provides for an anchoring pad having an adhesive carried by one side thereof which is compatible for use with living bodies. A flexible strap is provided having a layer of fastener material on one side thereof with a portion of said flexible strap attached to a side of the anchoring pad opposite the adhesive. The strap is adapted to fold across a catheter laid against the pad to secure the catheter to the pad by pressing the fastener material on the free end of the strap against the fastener material attached to the pad. Alternatively, a layer of fastener material can be carried by a side of the pad and a separate strap with fastener material on one side thereof provided to extend across a catheter laid on the pad. The fastener material may cover two spaced apart areas on the strap to define a hinge portion in between to faciliate folding of the strap over the catheter.

A channel is defined through the fastener material on either the pad or the strap portion for ready reception of the catheter.

In the preferred embodiment the adhesive is a pressure sensitive adhesive comprising a hemogenous blend of one or more water soluable and/or water swellable hydrocolloids dispersed in a viscous elastomeric substance. The fastener material comprises a plurality of spaced apart resilient and deformable plastic elements.

BRIEF DESCRIPTION OF THE DRAWINGS

FIG. 1 shows a top view of the preferred embodiment catheter support.

FIGS. 2A and 2B show top and side views of a sample of the preferred embodiment fastener material of the catheter support of FIG. 1 while FIG. 2C shows a top view of an alternate embodiment of the material of FIG. 2A.

FIG. 3 shows the catheter support of FIG. 1 applied to a human leg.

FIG. 4 is an enlarged isometric view of the preferred embodiment pad portion of the catheter support of FIG. 1.

DETAILED DESCRIPTION OF THE DRAWINGS

Referring now to FIG. 1, the preferred embodiment catheter support designated generally 100 comprises an anchoring pad designated generally 102 and flexible strap designated generally 106. One surface of pad 102 carries an adhesive which is compatible for use on a living body. The portion 108 of the flexible strap 106 is attached to side 110 of anchoring pad 102 opposite the side with the adhesive. The flexible strap 106 comprises a layer of fastener material 112 on one side thereof.

The fastener material 112 of flexible strap 106 can be made of any material or fabric adapted to fasten together by pressing together to form a frictional fit. An example of such a material sold under the name VELCRO TM comprises a nylon fabric that is adapted to be fastened to itself. In the preferred embodiment, the fastener material is a strip of plastic material which comprises a plurality of spaced apart resilient and deformable plastic elements which are arranged as in FIG. 2A in a planar array 200 forming rows and columns of elements 202, with equal spacing of elements 202 occurring in each row of the array being offset from an adjacent row by half the row elements spacing as shown by rows 204 and 206 in FIG. 2A. Shown in FIG. 2B is a side view of the elements 202 showing their curved shape. The elements 202 may be connected to a common flexible backing layer 210 which together with the elements form the strap 106. Alternatively the plastic elements 202 may be connected to one another individually at their corners as in FIG. 2C to form a flexible plastic strap of fastener material.

Referring now to FIG. 1, an area 120 has been cut out of the center portion of strap portion 108 connected to pad 102 to define a channel to receive the catheter tube 122. The elements 202 of the flexible material layer cover areas on the pad 102 on either side of channel 120.

Another area 130 has been cut out of the flexible material at the region where the free portion 109 of flexible strap 106 meets the attached portion 108. The free portion remains attached to the portion 108 via top and bottom connecting portions 132 and 134, respectively, formed from the common flexible backing layer 210.

Area 120 serves to provide a channel to make room for tube 122 when the free portion 109 of strap 106 is folded over the tube. The area 130 facilitates folding. Connecting portions 132 and 134 along with the open area 130 function as a hinge.

Alternatively, the area 120 could be formed in an appropriate portion of the free portion 109 of strap 106. Also, it is not necessary that the strap 106 be one continuous piece or that a common backing layer be used. For example, the array of elements as in FIG. 2C may be attached to side 110 of pad 102. A separate portion of the flexible strap 106 may be attached at one end to the side 110 of pad 102 or left completely unattached.

FIG. 3 shows a typical use for the catheter support 100 shown attached to a human leg 300. Prior to applying the pad 102, the skin is first cleansed. The pad is applied to the cleansed area by pressing the pad against the skin with the adhesive contacting the skin. The catheter tube is laid across the pad in the channel 120. Then the free end 109 of flexible strap 106 is folded over the tube and the free end is pressed against the fastener material attached to pad 102. It may also be desireable to provide a glue between the tube 122 and the channel to add further support and rigidity at the connecting point.

The choice of adhesive is very important in order to avoid localized irritation on the skin. The adhesive material can be formulated from any substance known to be compatible for use on the human body. Particular suitable adhesive compositions are pressure sensitive adhesive formulations that consist of a homogeneous blend of one or more water soluble or water swellable hydrocolloids dispersed in a viscous elastomeric substance such as polyisobutylene as disclosed by Chen in U.S. Pat. No. 3,339,546. Optionally, the adhesive composition can also include one or more cohesive strengthening agents described by Chen et al. in U.S. Pat. No. 4,192,785 or one or more hydratable natural or synthetic polymers as described by Pawelchak et al. in U.S. Pat. No. 4,393,080.

Referring to FIG. 4, a preferred embodiment pad designated generally 400 for use as pad 102 is shown comprising a thin water insoluble polymeric film 402 such as polyethylene with fastener material 112 attached thereto. Film 402 is sealable directly against a layer 404 of semi-open cell elastic or flexible foam as described by Pawelchak et al. in European Patent Application 92,999. The adhesive layer 406 of pressure sensitive skin-curative and skin-protective adhesive formulations as described above is bonded to the layer 404. Alternatively, the adhesive 406 can be bonded directly to the film 402. The film 402 serves to provide an outer protective layer which can be handled and touched and is a vehicle for carrying fastener material 112.

The fastener material 112 shown in FIG. 4 may comprise plastic elements 202 connected by the common backing layer 210 and be attached to the layer 402 by gluing or sewing etc., or the plurality of elements 202 with or without the backing layer 210 may be integrally formed with layer 402 by a hot meld adhesive process. For example, a layer of hot melted plastic in a fluid state is applied to film 402 of pad 400. Then, while still hot, the fastener material is pressed into the fluid until only the curved tops of the plastic elements remain above the hot plastic. The combination is allowed to cool.

A manufacturer of such suitable plastic material of resilient and deformable plastic elements as described above is Clements Industries, Inc., which manufactures a fastener material sold under the name of TACH-IT ™.

When the fastener material of the free end 109 of the strap 106 is pressed against the fastener material carried by the surface of the pad 102 the plastic elements 202 from each deform and move aside to allow the elements of each to partially interlace causing a frictional fit due to the resilient nature of the elements.

What is claimed is:

1. A catheter support for securing a catheter to a living body comprising:
   an anchoring pad having a body compatible adhesive carried by one side thereof;
   a flexible strap comprising a layer of fastener material on one side thereof, a portion of said flexible strap being attached to a side of said anchoring pad;
   said fastener material comprising a plurality of spaced apart resilient and deformable curved plastic elements which are arranged in a planar array with equal spacing of elements in each row of the array and with every other row offset from an adjacent row;
   said fastener material on said portion of strap attached to said pad having a channel formed therethrough for receiving said catheter;
   said fastener material divided into an area on said anchoring pad and a remaining area on said strap separated by a hinge area separate from said channel;
   said flexible strap adapted to fold at said hinge area across said catheter in said channel to secure it to said pad when said remaining area of fastener material is pressed together with said area on said anchoring pad.

2. The support of claim 1 wherein said fastener material carried by said pad is integrally formed with a surface of said pad.

3. The support of claim 2 wherein said fastener material is integrally formed with said pad by a hot meld adhesive.

4. The support of claim 1 wherein said adhesive is a pressure sensitive adhesive comprising a homogeneous blend of one or more water soluble and/or water swellable hydrocolloids dispersed in a viscous elastomeric substance.

5. The support of claim 4 wherein said adhesive pad further comprises a layer of semi-open cell elastic foam bonded to said layer of hydrocolloids.

* * * * *